US005952177A

United States Patent [19]

Bandman et al.

[11] Patent Number: 5,952,177

[45] Date of Patent: Sep. 14, 1999

[54] HUMAN CYTOSOLIC ISOCITRATE DEHYDROGENASE

[75] Inventors: Olga Bandman, Mountain View; Preeti Lal, Sunnyvale; Neil C. Corley, Mountain View; Janice Au-Young, Berkeley, all of Calif.

[73] Assignee: Incyte Pharmaceuticals, Inc., Palo Alto, Calif.

[21] Appl. No.: 08/984,171

[22] Filed: Dec. 3, 1997

[51] Int. Cl.[6] .............................. C12Q 1/68; C12P 21/06; C07H 21/02

[52] U.S. Cl. .......................... 435/6; 435/69.1; 435/320.1; 536/23.1

[58] Field of Search .......................... 536/23.1; 435/69.1, 435/320.1, 6

[56] References Cited

PUBLICATIONS

Jennings, G.T. et al., "Cytosolic NADP$^+$–dependent Isocitrate Dehydrogenase", *J. Biol. Chem.,* 269: 23128–23134, (1994).

Yadav, R.N. Singh and S.N. Singh, "Regulation of NAD–and NADP–Linked Isocitrate Dehydrogenase by Hydrocortisone in the Brain and Liver of Male Rats of Various Ages", *Biochim. Biophys. Acta.,* 633: 323–330, (1980).

Jennings, G.T. and P.M. Stevenson, "A study of the control of NADP$^+$–dependent isocitrate dehydrogenase activity during gonadotropin–induced development of the rat ovary", *Eur. J. Biochem.,* 198: 621–625, (1991).

Baumgart, E. et al., "Molecular characterization of the human peroxisomal branched–chain acyl–CoA oxidase: cDNA cloning, chromosomal assignment, tissue distribution, and evidence for the absence of the protein in Zellweger syndrome", *Proc. Natl. Acad. Sci. USA,* 93: 13748–13753, (1996).

Song, B.J., (Direct Submission), GenBank Sequence Database (Accession X69433), National Center for Biotechnology Information, National Library of Medicine, Bethesda, Maryland, 20894, (GI 872120; GI 872121) 1995.

Song, B.J., (Direct Submission), GenBank Sequence Database (Accession 872121), National Center for Biotechnology Information, National Library of Medicine, Bethesda, Maryland, 20894, (GI 872121) 1995.

Kim, Y.O. et al., (Direct Submission), GenBank Sequence Database (Accession U 7681 ), National Center for Biotechnology Information, National Library of Medicine, Bethesda, Maryland, 20894, (GI 706889, GI 706839 Jan. 26, 1996.

Kim, Y.O. et al., (Direct Submission), GenBank Sequence Database (Accession 706839), National Center for Biotechnology Information, National Library of Medicine, Bethesda, Maryland, 20894, (GI 706839) Jan. 25, 1996.

Kim, Y. et al., "Characterization of a cDNA clone for human NAD$^+$–specific isocitrate dehydrogenase α–subunit and structural comparison with its isoenzymes from different species", *Biochem. J.,* 308:63–68, (1995), (GI 706839).

Kullman et al. Genebank Accession No. U62389, Oct. 1996.

*Primary Examiner*—Paula K. Hutzell
*Assistant Examiner*—Lin Sun-Hoffman
*Attorney, Agent, or Firm*—Leanne C. Price; Incyte Pharmaceuticals Inc.

[57] ABSTRACT

The invention provides a human cytosolic isocitrate dehydrogenase (HCID) and polynucleotides which identify and encode HCID. The invention also provides expression vectors, host cells, antibodies, agonists, and antagonists. The invention also provides methods for treating disorders associated with expression of HCID.

9 Claims, 10 Drawing Sheets

```
                10          19          28          37          46          55
5' CCT GTG GTC CCG GGT TTC TGC AGA GTC TAC TTC AGA AGC GGA GGC ACT GGG AGT

                64          73          82          91         100         109
   CCG GTT TGG GAT TGC CAG GCT GTG GTT GTG AGT CTG AGC TTG TGA GCG GCT GTG

               118         127         136         145         154         163
   GCG CCC CAA CTC TTC GCC AGC ATA TCA TCC CGG CAG GCG ATA AAC TAC ATT CAG

               172         181         190         199         208         217
   TTG AGT CTG CAA GAC TGG GAG GAA CTG GGG TGA TAA GAA ATC TAT TCA CTG TCA

               226         235         244         253         262         271
   AGG TTT ATT GAA GTC AAA ATG TCC AAA AAA ATC AGT GGC GGT TCT GTG GTA GAG
                           M   S   K   K   I   S   G   G   S   V   V   E

               280         289         298         307         316         325
   ATG CAA GGA GAT GAA ATG ACA CGA ATC ATT TGG GAA TTG ATT AAA GAG AAA CTC
   M   Q   G   D   E   M   T   R   I   I   W   E   L   I   K   E   K   L
               334         343         352         361         370         379
   ATT TTT CCC TAC GTG GAA TTG GAT CTA CAT AGC TAT GAT TTA GGC ATA GAG AAT
   I   F   P   Y   V   E   L   D   L   H   S   Y   D   L   G   I   E   N
```

FIGURE 1A

```
                388         397         406         415         424         433
CGT GAT GCC ACC AAC GAC CAA GTC ACC AAG GAT GCT GCA GAA GCT ATA AAG AAG
R   D   A   T   N   D   Q   V   T   K   D   A   A   E   A   I   K   K

                442         451         460         469         478         487
CAT AAT GTT GGC GTC AAA TGT GCC ACT ATC ACT CCT GAT GAG AAG AGG GTT GAG
H   N   V   G   V   K   C   A   T   I   T   P   D   E   K   R   V   E

                496         505         514         523         532         541
GAG TTC AAG TTG AAA CAA ATG TGG AAA TCA CCA AAT GGC GCC ATA CGA AAT ATT
E   F   K   L   K   Q   M   W   K   S   P   N   G   A   I   R   N   I

                550         559         568         577         586         595
CTG GGT GGC ACG GTC TTC AGA GAA GCC ATT ATC TGC AAA AAT ATC CCC CGG CTT
L   G   G   T   V   F   R   E   A   I   I   C   K   N   I   P   R   L

                604         613         622         631         640         649
GTG AGT GGA TGG GTA AAA CCT ATC ATC ATA GGT CGT CAT GCT TAT GGG GAT CAA
V   S   G   W   V   K   P   I   I   I   G   R   H   A   Y   G   D   Q

                658         667         676         685         694         703
TAC AGA GCA ACT GAT TTT GTT GTT CCT GGG CCT GGA AAA GTA GAG ATA ACC TAC
Y   R   A   T   D   F   V   V   P   G   P   G   K   V   E   I   T   Y
```

FIGURE 1B

```
        712         721         730         739         748         757
ACA CCA AGT GAC GGA ACC CAA AAG GTG ACA TAC CTG GTA CAT AAC TTT GAA GAA
T   P   S   D   G   T   Q   K   V   T   Y   L   V   H   N   F   E   E

        766         775         784         793         802         811
GGT GGT GGT GTT GCC ATG GGG ATG TAT AAT CAA GAT AAG TCA ATT GAA GAT TTT
G   G   G   V   A   M   G   M   Y   N   Q   D   K   S   I   E   D   F

        820         829         838         847         856         865
GCA CAC AGT TCC TTC CAA ATG GCT CTG TCT AAG GGT TGG CCT TTG TAT CTG AGC
A   H   S   S   F   Q   M   A   L   S   K   G   W   P   L   Y   L   S

        874         883         892         901         910         919
ACC AAA AAC ACT ATT CTG AAG AAA TAT GAT GGG CGT TTT AAA GAC ATC TTT CAG
T   K   N   T   I   L   K   K   Y   D   G   R   F   K   D   I   F   Q

        928         937         946         955         964         973
GAG ATA TAT GAC AAG CAG TAC AAG TCC CAG TTT GAA GCT CAA AAG ATC TGG TAT
E   I   Y   D   K   Q   Y   K   S   Q   F   E   A   Q   K   I   W   Y

       982         991        1000        1009        1018        1027
GAG CAT AGG CTC ATC GAC GAC ATG GTG GCC CAA GCT ATG AAA TCA GAG GGA GGC
E   H   R   L   I   D   D   M   V   A   Q   A   M   K   S   E   G   G
```

FIGURE 1C

```
        1036         1045         1054         1063         1072         1081
TTC ATC TGG GCC TGT AAA AAC TAT GAT GGT GAC GTG CAG TCG GAC TCT GTG GCC
F   I   W   A   C   K   N   Y   D   G   D   V   Q   S   D   S   V   A

        1090         1099         1108         1117         1126         1135
CAA GGG TAT GGC TCT CTC GGC ATG ATG ACC AGC GTG CTG GTT TGT CCA GAT GGC
Q   G   Y   G   S   L   G   M   M   T   S   V   L   V   C   P   D   G

        1144         1153         1162         1171         1180         1189
AAG ACA GTA GAA GCA GAG GCT GCC CAC GGG ACT GTA ACC CGT CAC TAC CGC ATG
K   T   V   E   A   E   A   A   H   G   T   V   T   R   H   Y   R   M

        1198         1207         1216         1225         1234         1243
TAC CAG AAA GGA CAG GAG ACG TCC ACC AAT CCC ATT GCT TCC ATT TTT GCC TGG
Y   Q   K   G   Q   E   T   S   T   N   P   I   A   S   I   F   A   W

        1252         1261         1270         1279         1288         1297
ACC AGA GGG TTA GCC CAC AGA GCA AAG CTT GAT AAC AAT AAA GAG CTT GCC TTC
T   R   G   L   A   H   R   A   K   L   D   N   N   K   E   L   A   F

       1306         1315         1324         1333         1342         1351
TTT GCA AAT GCT TTG GAA GAA GTC TCT ATT GAG ACA ATT GAG GCT GGC TTC ATG
F   A   N   A   L   E   E   V   S   I   E   T   I   E   A   G   F   M
```

FIGURE 1D

```
        1360        1369        1378        1387        1396        1405
ACC AAG GAC TTG GCT GCT TGC ATT AAA GGT TTA CCC AAT GTG CAA CGT TCT GAC
T   K   D   L   A   A   C   I   K   G   L   P   N   V   Q   R   S   D

        1414        1423        1432        1441        1450        1459
TAC TTG AAT ACA TTT GAG TTC ATG GAT AAA CTT GGA GAA AAC TTG AAG ATC AAA
Y   L   N   T   F   E   F   M   D   K   L   G   E   N   L   K   I   K

        1468        1477        1486        1495        1504        1513
CTA GCT CAG GCC AAA CTT TAA GTT CAT ACC TGA GCT AAG AAG GAT AAT TGT CTT
L   A   Q   A   K   L

        1522        1531        1540        1549        1558        1567
TTG GTA ACT AGG TCT ACA GGT TTA CAT TTT TCT GTG TTA CAC TCA AGG ATA AAG

        1576        1585        1594        1603        1612        1621
GCA AAA TCA ATT TTG TAA TTT GTT TAG AAG CCA GAG TTT ATC TTT TCT ATA AGT

        1630        1639        1648        1657        1666        1675
TTA CAG CCT TTT TCT TAT ATA TAC AGT TAT TGC CAC CTT TGT GAA CAT GGC AAG

        1684        1693        1702        1711        1720        1729
GGA CTT TTT TAC AAT TTT TAT TTT ATT TTC TAG TAC CAG CCT AGG AAT TCG GTT
```

FIGURE 1E

```
       1738        1747        1756        1765        1774        1783
AGT ACT CAT TTG TAT TCA CTG TCA CTT TTT CTC ATG TTC TAA TTA TAA ATG ACC

       1792        1801        1810        1819        1828        1837
AAA ATC AAG ATT GCT CAA AAG GGT AAA TGA TAG CCA CAG TAT TGC TCC CTA AAA

       1846        1855        1864        1873        1882        1891
TAT GCA TAA AGT AGA AAT TCA CTG CCT TCC CCT CCT GTC CAT GAC CTT GGG CAC

       1900        1909        1918        1927        1936        1945
AGG GAA GTT CTG GTG TCA TAG ATA TCC CGT TTT GTG AGG TAG AGC TGT GCA TTA

       1954        1963        1972        1981        1990        1999
AAC TTG CAC ATG ACT GGA ACG AAG TAT GAG TGC AAC TCA AAT GTG TTG AAG ATA

       2008        2017        2026        2035        2044        2053
CTG CAG TCA TTT TTG TAA AGA CCT TGC TGA ATG TTT CCA ATA GAC TAA ATA CTG

       2062        2071        2080        2089        2098        2107
TTT AGG CCG CAG GAG AGT TTG GAA TCC GGA ATA AAT ACT ACC TGG AGG TTT GTC

       2116        2125        2134        2143        2152        2161
CTC TCC ATT TTT CTC TTT CTC CTC CTG GCC TGG CCT GAA TAT TAT ACT ACT CTA

      2170        2179        2188        2197        2206        2215
AAT AGC ATA TTT CAT CCA AGT GCA ATA ATG TAA GCT GAA TCT TTT TTG GAC TTC
```

FIGURE 1F

```
        2224        2233        2242        2251        2260        2269
TGC TGG CCT GTT TTA TTT CTT TTA TAT AAA TGT GAT TTC TCA GAA ATT GAT ATT

        2278        2287        2296        2305        2314        2323
AAA CAC TAT CTT ATC TTC TCC TGA ACT GTT GAT TTT AAT TAA AAT TAA GTG CTA

        2332        2341        2350        2359        2368        2377
ATT ACC AAA AAA AAA AAA AAA CCA AGA AAA AAC TAC AAA GAA TAA ATA CTA ATG

        2386        2395        2404        2413        2422        2431
GCC GAA GAA AGG GCG AGC GCG GAA GGG GAT GCA CGG TGG GGG GGC GGA GAG AAA

        2440        2449        2458        2467        2476        2485
AAG GGG GGG GGC CCC TCC AAA GGG GTC CCA GTC TTG GGA GCG CGG GGG TGG GGG

        2494        2503        2512        2521        2530        2539
GGG TTT AAG GCC CCT CCT AAG GGG GGC CCC CAC AAA TTT TGG TTT TTA CGA GGG

        2548        2557        2566        2575        2584        2593
GCC GGG GGG TTT TTA CCC AGC GGC GGG GAA TCG GGG GGA ACA CCC CGC GGG GGG

        2602        2611        2620        2629        2638        2647
GTT CCC CCC AGT TTA ATA GAG CGC CTT TGG GGG AGA AGT ACC GCC CCC TTT TGT

        2656        2665        2674        2683
GGA GAG TGT TGG GGG AGG ATT AAG GGG GAG AGG GGC C 3'
```

FIGURE 1G

```
1    M S - - - - - - - - - - - - - - - - - - - - - - - - - - - -  HCID
1    M A G Y L R V V R S L C R A S G S R P A W A P A A - - - L T  GI 872121
1    M A G - - - - - - - - - - - - - - - P A W I S K V S R L L G  GI 706839

3    - - - - - - - - - - - - - - - - K K I S G G - S V V E M Q G D E  HCID
28   A P T S Q E H P R R H Y A D K R I K V A K P V V E M D G D E  GI 872121
16   A F H N P K Q V T R G F T G - - - - - G V Q T V T L I P G D G  GI 706839

18   M T R I I W E L I K E K L I F P Y V E L D L H S Y D L G I E  HCID
58   M T R I I W Q F I K E K L I L P H V D I Q L K Y F D L G L P  GI 872121
42   I G P E I S A A V M K - - I F D A A K A P I Q W E E R N V T  GI 706839

48   N R D A T N D Q - - V T K D A A E A I K K H N V G V K C A T  HCID
88   N R D Q T D D Q - - V T I D S A L A T Q K Y S V A V K C A T  GI 872121
70   A I Q G P G G K W M I P S E A K E S M D K N K M G L K G P L  GI 706839

76   I T P D E K R V E E F K L K Q M W K S P N G A I R N I L G G  HCID
116  I T P D E A R V E E F K L K K M W K S P N G T I R N I L G G  GI 872121
100  K T P I A A G H P S M N L - - - - - - - - - L L R K T F D -  GI 706839

106  T V F R E A I I C K N I P R L V S G W V K P I I I G - R H A  HCID
146  T V F R E P I I C K N I P R L V P G W T K P I T I G - R H A  GI 872121
120  - L Y A N V R P C V S I E G Y K T P Y T D V N I V T I R E N  GI 706839

135  Y G D Q Y R A T D F V V P G P G K V E I T Y T P S D G T Q K  HCID
175  H G D Q Y K A T D F V A D R A G T F K M V F T P K D G S G V  GI 872121
149  T E G E Y S G I E H V I V D G V V Q S I K L I T E G A S - -  GI 706839
```

FIGURE 2A

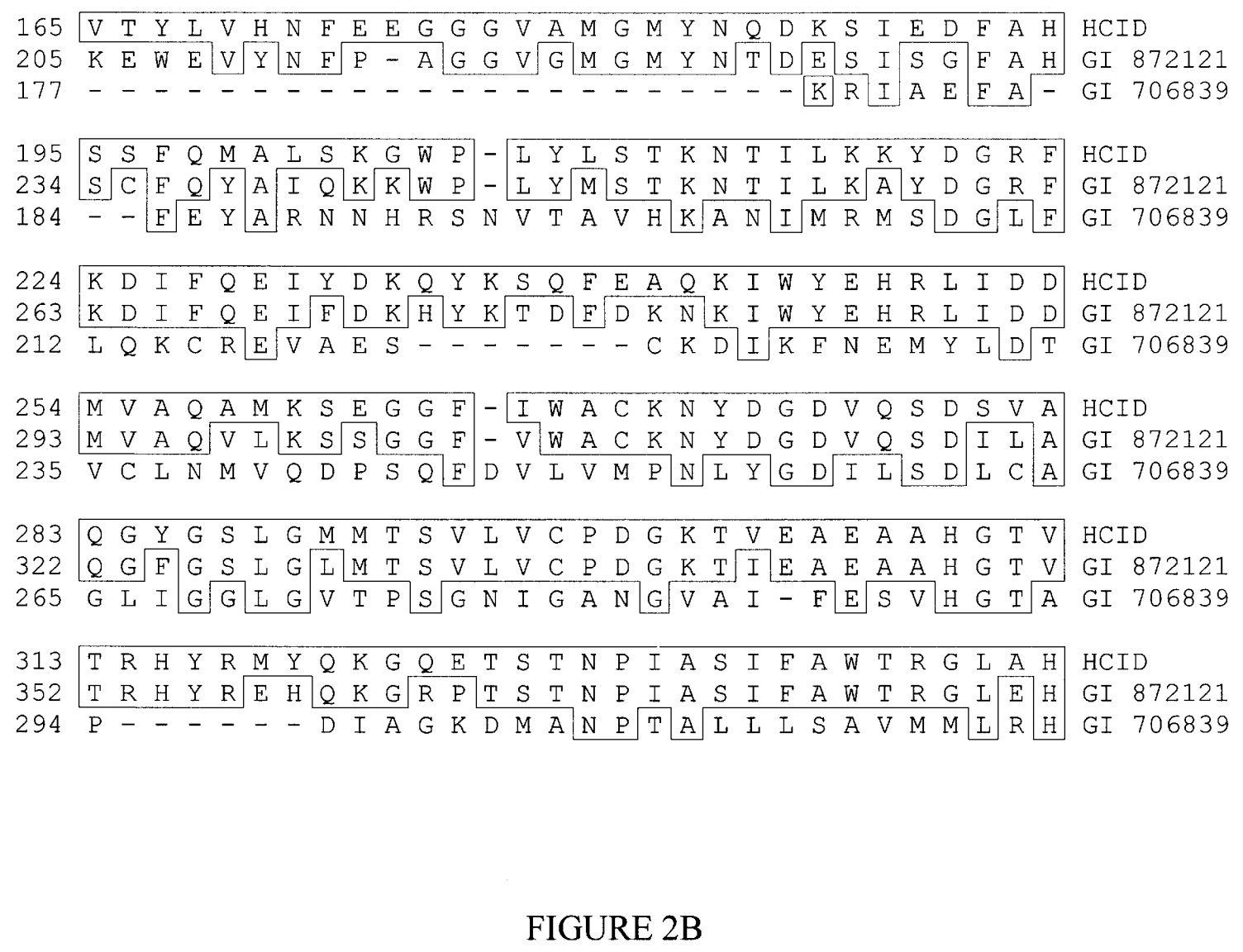

```
165 V T Y L V H N F E E G G G V A M G M Y N Q D K S I E D F A H HCID
205 K E W E V Y N F P - A G G V G M G M Y N T D E S I S G F A H GI 872121
177 - - - - - - - - - - - - - - - - - - - - - - K R I A E F A - GI 706839

195 S S F Q M A L S K G W P - L Y L S T K N T I L K K Y D G R F HCID
234 S C F Q Y A I Q K K W P - L Y M S T K N T I L K A Y D G R F GI 872121
184 - - F E Y A R N N H R S N V T A V H K A N I M R M S D G L F GI 706839

224 K D I F Q E I Y D K Q Y K S Q F E A Q K I W Y E H R L I D D HCID
263 K D I F Q E I F D K H Y K T D F D K N K I W Y E H R L I D D GI 872121
212 L Q K C R E V A E S - - - - - - - - C K D I K F N E M Y L D T GI 706839

254 M V A Q A M K S E G G F - I W A C K N Y D G D V Q S D S V A HCID
293 M V A Q V L K S S G G F - V W A C K N Y D G D V Q S D I L A GI 872121
235 V C L N M V Q D P S Q F D V L V M P N L Y G D I L S D L C A GI 706839

283 Q G Y G S L G M M T S V L V C P D G K T V E A E A A H G T V HCID
322 Q G F G S L G L M T S V L V C P D G K T I E A E A A H G T V GI 872121
265 G L I G G L G V T P S G N I G A N G V A I - F E S V H G T A GI 706839

313 T R H Y R M Y Q K G Q E T S T N P I A S I F A W T R G L A H HCID
352 T R H Y R E H Q K G R P T S T N P I A S I F A W T R G L E H GI 872121
294 P - - - - - - D I A G K D M A N P T A L L L S A V M M L R H GI 706839
```

FIGURE 2B

```
343 RAKLDNNKELAFFANALEEVSIETIEAG-F HCID
382 RGKLDGNQDLIRFAQMLEKVCVETVESG-A GI 872121
318 MGLFDH--------AARIEAACFATIKDGKS GI 706839

372 MTKDLAACIKGLPNVQRSD-YLNTFEFMDK HCID
411 MTKDLAGCIHGLSNVKLNEHFLNTMDFLDT GI 872121
341 LTKDLGGNAK-------------CSDFTEE GI 706839

401 LGENLKIKLAQAKL HCID
441 IKSNLDRALGRQ GI 872121
358 ICRRVK-DLD GI 706839
```

FIGURE 2C

```
                              SEQUENCE LISTING


(1) GENERAL INFORMATION:

   (iii) NUMBER OF SEQUENCES: 4


(2) INFORMATION FOR SEQ ID NO:1:

     (i) SEQUENCE CHARACTERISTICS:
          (A) LENGTH: 414 amino acids
          (B) TYPE: amino acid
          (C) STRANDEDNESS: single
          (D) TOPOLOGY: linear

   (vii) IMMEDIATE SOURCE:
          (A) LIBRARY: BRSTTUT03
          (B) CLONE: 1996789

         (xi) SEQUENCE DESCRIPTION: SEQ ID NO:1:

Met Ser Lys Lys Ile Ser Gly Gly Ser Val Val Glu Met Gln Gly Asp
 1              5                  10                  15

Glu Met Thr Arg Ile Ile Trp Glu Leu Ile Lys Glu Lys Leu Ile Phe
            20                  25                  30

Pro Tyr Val Glu Leu Asp Leu His Ser Tyr Asp Leu Gly Ile Glu Asn
        35                  40                  45

Arg Asp Ala Thr Asn Asp Gln Val Thr Lys Asp Ala Ala Glu Ala Ile
    50                  55                  60

Lys Lys His Asn Val Gly Val Lys Cys Ala Thr Ile Thr Pro Asp Glu
65                  70                  75                  80

Lys Arg Val Glu Glu Phe Lys Leu Lys Gln Met Trp Lys Ser Pro Asn
                85                  90                  95

Gly Ala Ile Arg Asn Ile Leu Gly Gly Thr Val Phe Arg Glu Ala Ile
            100                 105                 110

Ile Cys Lys Asn Ile Pro Arg Leu Val Ser Gly Trp Val Lys Pro Ile
        115                 120                 125
```

-continued

```
Ile Ile Gly Arg His Ala Tyr Gly Asp Gln Tyr Arg Ala Thr Asp Phe
    130                 135                 140

Val Val Pro Gly Pro Gly Lys Val Glu Ile Thr Tyr Thr Pro Ser Asp
145                 150                 155                 160

Gly Thr Gln Lys Val Thr Tyr Leu Val His Asn Phe Glu Glu Gly Gly
                165                 170                 175

Gly Val Ala Met Gly Met Tyr Asn Gln Asp Lys Ser Ile Glu Asp Phe
            180                 185                 190

Ala His Ser Ser Phe Gln Met Ala Leu Ser Lys Gly Trp Pro Leu Tyr
        195                 200                 205

Leu Ser Thr Lys Asn Thr Ile Leu Lys Lys Tyr Asp Gly Arg Phe Lys
    210                 215                 220

Asp Ile Phe Gln Glu Ile Tyr Asp Lys Gln Tyr Lys Ser Gln Phe Glu
225                 230                 235                 240

Ala Gln Lys Ile Trp Tyr Glu His Arg Leu Ile Asp Asp Met Val Ala
                245                 250                 255

Gln Ala Met Lys Ser Glu Gly Gly Phe Ile Trp Ala Cys Lys Asn Tyr
            260                 265                 270

Asp Gly Asp Val Gln Ser Asp Ser Val Ala Gln Gly Tyr Gly Ser Leu
        275                 280                 285

Gly Met Met Thr Ser Val Leu Val Cys Pro Asp Gly Lys Thr Val Glu
    290                 295                 300

Ala Glu Ala Ala His Gly Thr Val Thr Arg His Tyr Arg Met Tyr Gln
305                 310                 315                 320

Lys Gly Gln Glu Thr Ser Thr Asn Pro Ile Ala Ser Ile Phe Ala Trp
                325                 330                 335

Thr Arg Gly Leu Ala His Arg Ala Lys Leu Asp Asn Asn Lys Glu Leu
            340                 345                 350

Ala Phe Phe Ala Asn Ala Leu Glu Glu Val Ser Ile Glu Thr Ile Glu
        355                 360                 365

Ala Gly Phe Met Thr Lys Asp Leu Ala Ala Cys Ile Lys Gly Leu Pro
    370                 375                 380

Asn Val Gln Arg Ser Asp Tyr Leu Asn Thr Phe Glu Phe Met Asp Lys
385                 390                 395                 400

Leu Gly Glu Asn Leu Lys Ile Lys Leu Ala Gln Ala Lys Leu
                405                 410
```

(2) INFORMATION FOR SEQ ID NO:2:

(i) SEQUENCE CHARACTERISTICS:
(A) LENGTH: 2684 base pairs
(B) TYPE: nucleic acid
(C) STRANDEDNESS: single
(D) TOPOLOGY: linear (vii) IMMEDIATE SOURCE:
(A) LIBRARY: BRSTTUT03
(B) CLONE: 1996789

(xi) SEQUENCE DESCRIPTION: SEQ ID NO:2:

```
CCCTGTGGTC CCGGGTTTCT GCAGAGTCTA CTTCAGAAGC GGAGGCACTG GGAGTCCGGT    60

TTGGGATTGC CAGGCTGTGG TTGTGAGTCT GAGCTTGTGA GCGGCTGTGG CGCCCCAACT   120

CTTCGCCAGC ATATCATCCC GGCAGGCGAT AAACTACATT CAGTTGAGTC TGCAAGACTG   180

GGAGGAACTG GGGTGATAAG AAATCTATTC ACTGTCAAGG TTTATTGAAG TCAAAATGTC   240

CAAAAAAATC AGTGGCGGTT CTGTGGTAGA GATGCAAGGA GATGAAATGA CACGAATCAT   300
```

-continued

```
TTGGGAATTG ATTAAAGAGA AACTCATTTT TCCCTACGTG GAATTGGATC TACATAGCTA   360
TGATTTAGGC ATAGAGAATC GTGATGCCAC CAACGACCAA GTCACCAAGG ATGCTGCAGA   420
AGCTATAAAG AAGCATAATG TTGGCGTCAA ATGTGCCACT ATCACTCCTG ATGAGAAGAG   480
GGTTGAGGAG TTCAAGTTGA AACAAATGTG GAAATCACCA AATGGCGCCA TACGAAATAT   540
TCTGGGTGGC ACGGTCTTCA GAGAAGCCAT TATCTGCAAA AATATCCCCC GGCTTGTGAG   600
TGGATGGGTA AAACCTATCA TCATAGGTCG TCATGCTTAT GGGGATCAAT ACAGAGCAAC   660
TGATTTTGTT GTTCCTGGGC CTGGAAAAGT AGAGATAACC TACACACCAA GTGACGGAAC   720
CCAAAAGGTG ACATACCTGG TACATAACTT TGAAGAAGGT GGTGGTGTTG CCATGGGGAT   780
GTATAATCAA GATAAGTCAA TTGAAGATTT TGCACACAGT TCCTTCCAAA TGGCTCTGTC   840
TAAGGGTTGG CCTTTGTATC TGAGCACCAA AAACACTATT CTGAAGAAAT ATGATGGGCG   900
TTTTAAAGAC ATCTTTCAGG AGATATATGA CAAGCAGTAC AAGTCCCAGT TTGAAGCTCA   960
AAAGATCTGG TATGAGCATA GGCTCATCGA CGACATGGTG GCCCAAGCTA TGAAATCAGA  1020
GGGAGGCTTC ATCTGGGCCT GTAAAAACTA TGATGGTGAC GTGCAGTCGG ACTCTGTGGC  1080
CCAAGGGTAT GGCTCTCTCG GCATGATGAC CAGCGTGCTG GTTTGTCCAG ATGGCAAGAC  1140
AGTAGAAGCA GAGGCTGCCC ACGGGACTGT AACCCGTCAC TACCGCATGT ACCAGAAAGG  1200
ACAGGAGACG TCCACCAATC CCATTGCTTC CATTTTTGCC TGGACCAGAG GGTTAGCCCA  1260
CAGAGCAAAG CTTGATAACA ATAAAGAGCT TGCCTTCTTT GCAAATGCTT TGGAAGAAGT  1320
CTCTATTGAG ACAATTGAGG CTGGCTTCAT GACCAAGGAC TTGGCTGCTT GCATTAAAGG  1380
TTTACCCAAT GTGCAACGTT CTGACTACTT GAATACATTT GAGTTCATGG ATAAACTTGG  1440
AGAAAACTTG AAGATCAAAC TAGCTCAGGC CAAACTTTAA GTTCATACCT GAGCTAAGAA  1500
GGATAATTGT CTTTTGGTAA CTAGGTCTAC AGGTTTACAT TTTTCTGTGT TACACTCAAG  1560
GATAAAGGCA AAATCAATTT TGTAATTTGT TTAGAAGCCA GAGTTTATCT TTTCTATAAG  1620
TTTACAGCCT TTTTCTTATA TATACAGTTA TTGCCACCTT TGTGAACATG GCAAGGGACT  1680
TTTTTACAAT TTTTATTTTA TTTTCTAGTA CCAGCCTAGG AATTCGGTTA GTACTCATTT  1740
GTATTCACTG TCACTTTTTC TCATGTTCTA ATTATAAATG ACCAAAATCA AGATTGCTCA  1800
AAAGGGTAAA TGATAGCCAC AGTATTGCTC CCTAAAATAT GCATAAAGTA GAAATTCACT  1860
GCCTTCCCCT CCTGTCCATG ACCTTGGGCA CAGGGAAGTT CTGGTGTCAT AGATATCCCG  1920
TTTTGTGAGG TAGAGCTGTG CATTAAACTT GCACATGACT GGAACGAAGT ATGAGTGCAA  1980
CTCAAATGTG TTGAAGATAC TGCAGTCATT TTTGTAAAGA CCTTGCTGAA TGTTTCCAAT  2040
AGACTAAATA CTGTTTAGGC CGCAGGAGAG TTTGGAATCC GGAATAAATA CTACCTGGAG  2100
GTTTGTCCTC TCCATTTTTC TCTTTCTCCT CCTGGCCTGG CCTGAATATT ATACTACTCT  2160
AAATAGCATA TTTCATCCAA GTGCAATAAT GTAAGCTGAA TCTTTTTTGG ACTTCTGCTG  2220
GCCTGTTTTA TTTCTTTTAT ATAAATGTGA TTTCTCAGAA ATTGATATTA AACACTATCT  2280
TATCTTCTCC TGAACTGTTG ATTTTAATTA AAATTAAGTG CTAATTACCA AAAAAAAAAA  2340
AAAACCAAGA AAAAACTACA AAGAATAAAT ACTAATGGCC GAAGAAAGGG CGAGCGCGGA  2400
AGGGGATGCA CGGTGGGGGG GCGGAGAGAA AAAGGGGGGG GGCCCCTCCA AAGGGGTCCC  2460
AGTCTTGGGA GCGCGGGGGT GGGGGGGGTT TAAGGCCCCT CCTAAGGGGG GCCCCCACAA  2520
ATTTTGGTTT TTACGAGGGG CCGGGGGGTT TTTACCCAGC GGCGGGGAAT CGGGGGGAAC  2580
ACCCCGCGGG GGGGTTCCCC CCAGTTTAAT AGAGCGCCTT TGGGGGAGAA GTACCGCCCC  2640
CTTTTGTGGA GAGTGTTGGG GGAGGATTAA GGGGGAGAGG GGCC                   2684
```

(2) INFORMATION FOR SEQ ID NO:3:

(i) SEQUENCE CHARACTERISTICS:
(A) LENGTH: 452 amino acids
(B) TYPE: amino acid
(C) STRANDEDNESS: single
(D) TOPOLOGY: linear (vii) IMMEDIATE SOURCE:
(A) LIBRARY: GenBank
(B) CLONE: 872121

(xi) SEQUENCE DESCRIPTION: SEQ ID NO:3:

```
Met Ala Gly Tyr Leu Arg Val Val Arg Ser Leu Cys Arg Ala Ser Gly
 1               5                  10                  15

Ser Arg Pro Ala Trp Ala Pro Ala Ala Leu Thr Ala Pro Thr Ser Gln
            20                  25                  30

Glu His Pro Arg Arg His Tyr Ala Asp Lys Arg Ile Lys Val Ala Lys
        35                  40                  45

Pro Val Val Glu Met Asp Gly Asp Glu Met Thr Arg Ile Ile Trp Gln
    50                  55                  60

Phe Ile Lys Glu Lys Leu Ile Leu Pro His Val Asp Ile Gln Leu Lys
65                  70                  75                  80

Tyr Phe Asp Leu Gly Leu Pro Asn Arg Asp Gln Thr Asp Asp Gln Val
                85                  90                  95

Thr Ile Asp Ser Ala Leu Ala Thr Gln Lys Tyr Ser Val Ala Val Lys
            100                 105                 110

Cys Ala Thr Ile Thr Pro Asp Glu Ala Arg Val Glu Glu Phe Lys Leu
        115                 120                 125

Lys Lys Met Trp Lys Ser Pro Asn Gly Thr Ile Arg Asn Ile Leu Gly
    130                 135                 140

Gly Thr Val Phe Arg Glu Pro Ile Ile Cys Lys Asn Ile Pro Arg Leu
145                 150                 155                 160

Val Pro Gly Trp Thr Lys Pro Ile Thr Ile Gly Arg His Ala His Gly
                165                 170                 175

Asp Gln Tyr Lys Ala Thr Asp Phe Val Ala Asp Arg Ala Gly Thr Phe
            180                 185                 190

Lys Met Val Phe Thr Pro Lys Asp Gly Ser Gly Val Lys Glu Trp Glu
        195                 200                 205

Val Tyr Asn Phe Pro Ala Gly Gly Val Gly Met Gly Met Tyr Asn Thr
    210                 215                 220

Asp Glu Ser Ile Ser Gly Phe Ala His Ser Cys Phe Gln Tyr Ala Ile
225                 230                 235                 240

Gln Lys Lys Trp Pro Leu Tyr Met Ser Thr Lys Asn Thr Ile Leu Lys
                245                 250                 255

Ala Tyr Asp Gly Arg Phe Lys Asp Ile Phe Gln Glu Ile Phe Asp Lys
            260                 265                 270

His Tyr Lys Thr Asp Phe Asp Lys Asn Lys Ile Trp Tyr Glu His Arg
        275                 280                 285

Leu Ile Asp Asp Met Val Ala Gln Val Leu Lys Ser Ser Gly Gly Phe
    290                 295                 300

Val Trp Ala Cys Lys Asn Tyr Asp Gly Asp Val Gln Ser Asp Ile Leu
305                 310                 315                 320

Ala Gln Gly Phe Gly Ser Leu Gly Leu Met Thr Ser Val Leu Val Cys
                325                 330                 335

Pro Asp Gly Lys Thr Ile Glu Ala Glu Ala Ala His Gly Thr Val Thr
            340                 345                 350
```

-continued

```
Arg His Tyr Arg Glu His Gln Lys Gly Arg Pro Thr Ser Thr Asn Pro
        355                 360                 365

Ile Ala Ser Ile Phe Ala Trp Thr Arg Gly Leu Glu His Arg Gly Lys
    370                 375                 380

Leu Asp Gly Asn Gln Asp Leu Ile Arg Phe Ala Gln Met Leu Glu Lys
385                 390                 395                 400

Val Cys Val Glu Thr Val Glu Ser Gly Ala Met Thr Lys Asp Leu Ala
                405                 410                 415

Gly Cys Ile His Gly Leu Ser Asn Val Lys Leu Asn Glu His Phe Leu
            420                 425                 430

Asn Thr Met Asp Phe Leu Asp Thr Ile Lys Ser Asn Leu Asp Arg Ala
        435                 440                 445

Leu Gly Arg Gln
    450
```

(2) INFORMATION FOR SEQ ID NO:4:

(i) SEQUENCE CHARACTERISTICS:
(A) LENGTH: 366 amino acids
(B) TYPE: amino acid
(C) STRANDEDNESS: single
(D) TOPOLOGY: linear (vii) IMMEDIATE SOURCE:
(A) LIBRARY: GenBank
(B) CLONE: 706839

(xi) SEQUENCE DESCRIPTION: SEQ ID NO:4:

```
Met Ala Gly Pro Ala Trp Ile Ser Lys Val Ser Arg Leu Leu Gly Ala
 1               5                  10                  15

Phe His Asn Pro Lys Gln Val Thr Arg Gly Phe Thr Gly Gly Val Gln
            20                  25                  30

Thr Val Thr Leu Ile Pro Gly Asp Gly Ile Gly Pro Glu Ile Ser Ala
        35                  40                  45

Ala Val Met Lys Ile Phe Asp Ala Ala Lys Ala Pro Ile Gln Trp Glu
    50                  55                  60

Glu Arg Asn Val Thr Ala Ile Gln Gly Pro Gly Gly Lys Trp Met Ile
65                  70                  75                  80

Pro Ser Glu Ala Lys Glu Ser Met Asp Lys Asn Lys Met Gly Leu Lys
                85                  90                  95

Gly Pro Leu Lys Thr Pro Ile Ala Ala Gly His Pro Ser Met Asn Leu
            100                 105                 110

Leu Leu Arg Lys Thr Phe Asp Leu Tyr Ala Asn Val Arg Pro Cys Val
        115                 120                 125

Ser Ile Glu Gly Tyr Lys Thr Pro Tyr Thr Asp Val Asn Ile Val Thr
    130                 135                 140

Ile Arg Glu Asn Thr Glu Gly Glu Tyr Ser Gly Ile Glu His Val Ile
145                 150                 155                 160

Val Asp Gly Val Val Gln Ser Ile Lys Leu Ile Thr Glu Gly Ala Ser
                165                 170                 175

Lys Arg Ile Ala Glu Phe Ala Phe Glu Tyr Ala Arg Asn Asn His Arg
            180                 185                 190

Ser Asn Val Thr Ala Val His Lys Ala Asn Ile Met Arg Met Ser Asp
        195                 200                 205

Gly Leu Phe Leu Gln Lys Cys Arg Glu Val Ala Glu Ser Cys Lys Asp
    210                 215                 220

Ile Lys Phe Asn Glu Met Tyr Leu Asp Thr Val Cys Leu Asn Met Val
```

-continued

```
225                 230                 235                 240

Gln Asp Pro Ser Gln Phe Asp Val Leu Val Met Pro Asn Leu Tyr Gly
                245                 250                 255

Asp Ile Leu Ser Asp Leu Cys Ala Gly Leu Ile Gly Gly Leu Gly Val
            260                 265                 270

Thr Pro Ser Gly Asn Ile Gly Ala Asn Gly Val Ala Ile Phe Glu Ser
        275                 280                 285

Val His Gly Thr Ala Pro Asp Ile Ala Gly Lys Asp Met Ala Asn Pro
    290                 295                 300

Thr Ala Leu Leu Leu Ser Ala Val Met Met Leu Arg His Met Gly Leu
305                 310                 315                 320

Phe Asp His Ala Ala Arg Ile Glu Ala Ala Cys Phe Ala Thr Ile Lys
                325                 330                 335

Asp Gly Lys Ser Leu Thr Lys Asp Leu Gly Gly Asn Ala Lys Cys Ser
            340                 345                 350

Asp Phe Thr Glu Glu Ile Cys Arg Arg Val Lys Asp Leu Asp
        355                 360                 365
```

HUMAN CYTOSOLIC ISOCITRATE DEHYDROGENASE

FIELD OF THE INVENTION

This invention relates to nucleic acid and amino acid sequences of a human cytosolic isocitrate dehydrogenase and to the use of these sequences in the diagnosis, prevention, and treatment of cancer, reproductive disorders, and disorders of peroxisome metabolism.

BACKGROUND OF THE INVENTION

Isocitrate dehydrogenase (ID) catalyzes the conversion of isocitrate to α-ketoglutarate, a substrate of the citric acid cycle. In doing so, ID also captures the reducing power of the reaction by transferring electrons from isocitrate to an electron acceptor. In this way, ID participates in generating ATP to power a cell's numerous energy-requiring reactions, and harnesses high energy electrons for subsequent oxidation/reduction reactions.

Eukaryotic organisms contain three isocitrate dehydrogenases (IDs), representing a well-conserved family of enzymes. Though there may be low overall sequence homology within this family of enzymes, there is a sequence of 20 amino acids near the C-terminal region called the isocitrate dehydrogenase signature sequence, which is highly conserved between family members. The three eukaryotic IDs fill different physiological roles, a requirement which is reflected in their localization in different cellular compartments, and in their interaction with distinct electron acceptors. Two of these IDs are associated with mitochondria but interact with different electron acceptors. One mitochondrial ID interacts specifically with the electron acceptor nicotinamide adenine dinucleotide (NAD), and is termed NAD-dependent, while the other mitochondrial ID interacts specifically with nicotinamide adenine dinucleotide phosphate (NADP), and is termed NADP-dependent. The third ID is termed cytosolic (cytosolic isocitrate dehydrogenase, CID), but may be found either in the cytosol or in peroxisomes. CID is NADP-dependent. Differences in functional roles of IDs relate to differences in electron acceptor requirements. NAD is the major electron acceptor involved in generation of ATP via oxidative phosphorylation in mitochondria. NADP is the major electron acceptor involved in biosynthetic pathways requiring reducing power, including the synthesis of cholesterol and bile acids, oxidation of D-amino acids, fatty acids and polyamines, and peroxide-based metabolism. Thus, ID couples the oxidative decarboxylation of isocitrate to the generation of molecules essential for the production of cellular energy (NAD) and for various biosynthetic reactions (NADP) (Jennings, G. T. et al. (1994) J Biol Chem 269: 23128–34).

The activity of cytosolic isocitrate dehydrogenase (CID) varies from tissue to tissue. In reproductive tissue such as the ovary and mammary gland, and in the liver, CID activity is high, while in heart and skeletal muscle CID activity is low. Liver tissue and reproductive tissues have high levels of NADP-dependent biosynthetic reactions. This tissue-specific difference in CID activity reflects the role of CID in generating NADP for biosynthetic reactions. In addition, CID activity is regulated during development. In the rat, CID activity is maximal in immature brain but decreases with age, while in the liver, where CID activity is highest of any tissue, the converse is true (Yadav, R. N. and Singh, S. N. (1980) Biochim Biophys Acta 633: 323–30). CID activity is also regulated by hormones. The activity of CID was dramatically increased in gonadotropin-induced development of the immature rat ovary. Similarly, the enzyme's activity is increased in the mammary gland at the onset of lactation. The regulation of CID activity by hormones and by cellular differentiation in reproductive tissues indicates a role for CID in cancer and disorders of the reproductive system (Jennings, G. T. and Stevenson, P. M. (1991) Eur J Biochem 198: 621–25).

Peroxisomes are membrane-delineated organelles found in nearly all eukaryotic cells. The interior, or matrix, of the peroxisome contains at least fifty enzymes, most of which are targeted to the peroxisome by a microbodies C-terminal targeting signal, typically SKL (ser-lys-leu). Peroxisomal enzymes catalyze a variety of metabolic reactions involved in reductive biosynthetic pathways, such as the synthesis of cholesterol and bile acids, the oxidation of D-amino acids, fatty acids and polyamines, and peroxide-based metabolism. These various metabolic processes require reducing power in the form of NADP. Thus, defects in the generation of NADP by CID in peroxisomes can result in disorders associated with peroxisome metabolism (Baumgart, E. et al. (1996) Proc Natl Acad Sci 93: 13748–53).

The discovery of a new human cytosolic isocitrate dehydrogenase and the polynucleotides encoding it satisfies a need in the art by providing new compositions which are useful in the diagnosis, prevention and treatment of cancer, reproductive disorders, and disorders of peroxisome metabolism.

SUMMARY OF THE INVENTION

The invention features a substantially purified polypeptide, human cytosolic isocitrate dehydrogenase (HCID), comprising the amino acid sequence of SEQ ID NO:1 or a fragment of SEQ ID NO:1.

The invention further provides a substantially purified variant of HCID having at least 90% amino acid identity to the amino acid sequence of SEQ ID NO:1 or a fragment of SEQ ID NO:1. The invention also provides an isolated and purified polynucleotide sequence encoding the polypeptide comprising the amino acid sequence of SEQ ID NO:1 or a fragment of SEQ ID NO:1. The invention also includes an isolated and purified polynucleotide variant having at least 90% polynucleotide identity to the polynucleotide sequence encoding the polypeptide comprising the amino acid sequence of SEQ ID NO:1 or a fragment of SEQ ID NO:1.

Additionally, the invention provides a composition comprising a polynucleotide sequence encoding the polypeptide comprising the amino acid sequence of SEQ ID NO:1 or a fragment of SEQ ID NO:1. The invention further provides an isolated and purified polynucleotide sequence which hybridizes under stringent conditions to the polynucleotide sequence encoding the polypeptide comprising the amino acid sequence of SEQ ID NO:1 or a fragment of SEQ ID NO:1, as well as an isolated and purified polynucleotide sequence which is complementary to the polynucleotide sequence encoding the polypeptide comprising the amino acid sequence of SEQ ID NO:1 or a fragment of SEQ ID NO:1.

The invention also provides an isolated and purified polynucleotide sequence comprising SEQ ID NO:2 or a fragment of SEQ ID NO:2, and an isolated and purified polynucleotide variant having at least 90% polynucleotide identity to SEQ ID NO:2 or a fragment of SEQ ID NO:2. The invention also provides an isolated and purified polynucleotide sequence which is complementary to the polynucleotide sequence comprising SEQ ID NO:2 or a fragment of SEQ ID NO:2.

The invention further provides an expression vector containing at least a fragment of SEQ ID:. In another aspect, the expression vector containing the polynucleotide sequence is contained within a host cell.

The invention also provides a method for producing a polypeptide comprising the amino acid sequence of SEQ ID NO:1 or a fragment of SEQ ID NO:1, the method comprising the steps of: (a) culturing the host cell containing an expression vector containing at least a fragment of a polynucleotide sequence encoding HCID under conditions suitable for the expression of the polypeptide; and (b) recovering the polypeptide from the host cell culture.

The invention also provides a pharmaceutical composition comprising a substantially purified HCID having the amino acid sequence of SEQ ID NO:1 or a fragment of SEQ ID NO:1 in conjunction with a suitable pharmaceutical carrier.

The invention further includes a purified antibody which binds to a polypeptide comprising the amino acid sequence of SEQ ID NO:1 or a fragment of SEQ ID NO:1, as well as a purified agonist and a purified antagonist of the polypeptide.

The invention also provides a method for treating or preventing a cancer, the method comprising administering to a subject in need of such treatment an effective amount of an antagonist of HCID.

The invention also provides a method for treating or preventing a reproductive disorder, the method comprising administering to a subject in need of such treatment an effective amount of an agonist of HCID.

The invention also provides a method for treating or preventing a reproductive disorder, the method comprising administering to a subject in need of such treatment an effective amount of a pharmaceutical composition comprising substantially purified HCID.

The invention also provides a method for treating or preventing a reproductive disorder, the method comprising administering to a subject in need of such treatment an effective amount of an antagonist of HCID.

The invention also provides a method for treating or preventing a disorder of peroxisome metabolism, the method comprising administering to a subject in need of such treatment an effective amount of an agonist of HCID.

The invention also provides a method for treating or preventing a peroxisome metabolism disorder, the method comprising administering to a subject in need of such treatment an effective amount of a pharmaceutical composition comprising substantially purified HCID.

The invention also provides a method for detecting a polynucleotide encoding HCID in a biological sample containing nucleic acid material, the method comprising the steps of: (a) hybridizing the complement of the polynucleotide sequence which encodes the polypeptide comprising SEQ ID NO:1 or a fragment of SEQ ID NO:1 to the nucleic acid material of the biological sample, thereby forming a hybridization complex; and (b) detecting the hybridization complex, wherein the presence of the hybridization complex correlates with the presence of a polynucleotide encoding HCID in the biological sample. In one aspect, the nucleic acid material of the biological sample is amplified by the polymerase chain reaction prior to the hybridizing step.

BRIEF DESCRIPTION OF THE FIGURES

FIGS. 1A, 1B, 1C, 1D, 1E, 1F and 1G show the amino acid sequence (SEQ ID NO:1) and nucleic acid sequence (SEQ ID NO:2) of HCID. The alignment was produced using MACDNASIS PRO software (Hitachi Software Engineering Co. Ltd. San Bruno, Calif.).

FIGS. 2A, 2B and 2C show the amino acid sequence alignments among HCID (SEQ ID NO:1), human mitochondrial NADP-dependent isocitrate dehydrogenase (mPICD) (GI 872121; SEQ ID NO:3), and human mitochondrial NAD-dependent isocitrate dehydrogenase (mICD) (GI 706839; SEQ ID NO:4), produced using the multisequence alignment program of DNASTAR software (DNASTAR Inc, Madison Wis.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

HCID, as used herein, refers to the amino acid sequences of substantially purified HCID obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to HCID, increases or prolongs the duration of the effect of HCID. Agonists may include proteins, nucleic acids, carbohydrates, or any other molecules which bind to and modulate the effect of HCID.

An "allele" or "allelic sequence", as used herein, is an alternative form of the gene encoding HCID. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding HCID as used herein include those with deletions, insertions, or substitutions of different nucleotides resulting in a polynucleotide that encodes the same or a functionally equivalent HCID. Included within this definition are polymorphisms which may or may not be readily detectable using a particular oligonucleotide probe of the polynucleotide encoding HCID, and improper or unexpected hybridization to alleles, with a locus other than the normal chromosomal locus for the polynucleotide sequence encoding HCID. The encoded protein may also be "altered" and contain deletions, insertions, or substitutions of amino acid residues which produce a silent change and result in a functionally equivalent HCID. Deliberate amino acid substitutions may be made on the basis of similarity in polarity, charge, solubility, hydrophobicity, hydrophilicity, and/or the amphipathic nature of the residues as long as the biological or immunological activity of HCID is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence" as used herein refers to an oligopeptide, peptide, polypeptide, or protein sequence, and fragment thereof, and to naturally occurring or synthetic molecules. Fragments of HCID are preferably about 5 to about 15 amino acids in length and retain the biological activity or the immunological activity of HCID. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "antagonist" as used herein, refers to a molecule which, when bound to HCID, decreases the amount or the duration of the effect of the biological or immunological activity of HCID. Antagonists may include proteins, nucleic acids, carbohydrates, antibodies or any other molecules which decrease the effect of HCID.

As used herein, the term "antibody" refers to intact molecules as well as fragments thereof, such as Fab, $F(ab')_2$, and Fv, which are capable of binding the epitopic determinant. Antibodies that bind HCID polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic HCID, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein refers broadly to any composition containing the given polynucleotide sequence. The composition may comprise a dry formulation or an aqueous solution. Compositions comprising polynucleotide sequences encoding HCID (SEQ ID NO:1) or fragments thereof (e.g., SEQ ID NO:2 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW fragment assembly system, GCG, Madison, Wis.). Some sequences have been both extended and assembled to produce the consensus sequence .

The term "correlates with expression of a polynucleotide", as used herein, indicates that the detection of the presence of ribonucleic acid that is similar to SEQ ID NO:2 by northern analysis is indicative of the presence of mRNA encoding HCID in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to HCID or the encoded HCID. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides synthesized on a substrate, such as paper, nylon or other type of membrane, filter, chip, glass slide, or any other suitable solid support.

The term "modulate", as used herein, refers to a change in the activity of HCID. For example, modulation may cause an increase or a decrease in protein activity, binding characteristics, or any other biological, functional or immunological properties of HCID.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers","primers", "oligomers", and "probes", as commonly defined in the art.

"Peptide nucleic acid" (PNA) as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of SEQ ID NO:1" encompasses the full-length HCID and fragments thereof.

The term "sample", as used herein, is used in its broadest sense. A biological sample suspected of containing nucleic acid encoding HCID, or fragments thereof, or HCID itself may comprise a bodily fluid, extract from a cell, chromosome, organelle, or membrane isolated from a cell, a cell, genomic DNA, RNA, or cDNA(in solution or bound to a solid support, a tissue, a tissue print, and the like.

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

As used herein, the term "stringent conditions" refers to conditions which permit hybridization between polynucleotide sequences and the claimed polynucleotide sequences. Suitably stringent conditions can be defined by, for example, the concentrations of salt and/or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5X SSPE, 0.3% SDS, and 200 $\mu$g/ml sheared and denatured salmon sperm DNA. Hybridization could occur under reduced stringency conditions as described above, but in 35% formamide or/and at a reduced temperature of 35° C. Variations on the above ranges and conditions are well known in the art.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of HCID, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The Invention

The invention is based on the discovery of a new human cytosolic isocitrate dehydrogenase (hereinafter referred to as "HCID"), the polynucleotides encoding HCID, and the use of these compositions for the diagnosis, prevention, or treatment of cancer, reproductive disorders, and disorders of peroxisome metabolism.

Nucleic acids encoding the HCID of the present invention were first identified in Incyte Clone 1996789 from the breast carcinoma CDNA library (BRSTTUT03) using a computer search for amino acid sequence alignments. A consensus sequence, SEQ ID NO:2, was derived from the following overlapping and/or extended nucleic acid sequences: Incyte Clones 1996789 (BRSTTUT03), 259754 (HNT2RAT01), 771611 (COLNCRT01), 534197 (BRAINOT03) and 1981403 (LUNGTUT03).

In one embodiment, the invention encompasses a polypeptide comprising the amino acid sequence of SEQ ID NO:1, as shown in FIGS. 1A, 1B, 1C, 1D, 1E, 1F and 1G. HCID is 414 amino acids in length and has an isocitrate dehydrogenase signature sequence from residues $N_{271}$ to $M_{290}$. HCID has a microbodies C-terminal targeting signal sequence, consisting of residues $A_{412}$, $K_{413}$ and $L_{414}$. HCID has potential cAMP/cGMP-dependent protein kinase phosphorylation site at residue $S_6$, potential protein kinase C phosphorylation sites at $S_2$, $T_{162}$, and $S_{210}$, and potential casein kinase II phosphorylation sites at residues $S_9$, $T_{77}$, $T_{157}$, $S_{188}$ and $S_{237}$. As shown in FIGS. 2A, 2B, and 2C, HCID has chemical and structural homology with mPICD (GI 872121; SEQ ID NO:3) and with mICD (GI 706839; SEQ ID NO:4). In particular, HCID and mPICD share 66% identity while HCID and mICD share 13% identity. Northern analysis shows the expression of this sequence in various cells and tissues, at least 53% of which are associated with cancerous tissues, and at least 32% of which are associated with reproductive organs or cell lines derived from reproductive organs. Of particular note is the expression of HCID in breast tumors, prostate tumors, and ovarian tumors.

The invention also encompasses HCID variants. A preferred HCID variant is one having at least about 80%, more preferably at least about 90%, and most preferably at least about 95% amino acid sequence identity to the HCID amino acid sequence.

The invention also encompasses a polynucleotide sequence which encodes HCID. Accordingly, any nucleic acid sequence which encodes the amino acid sequence of HCID can be used to produce recombinant molecules which express HCID. In a particular embodiment, the invention encompasses the polynucleotide comprising the nucleic acid sequence of SEQ ID NO:2 as shown in FIGS. 1A, 1B, 1C, 1D, 1E, 1F, and 1G.

The invention also encompasses a variant of a polynucleotide sequence encoding HCID. In particular, such a variant polynucleotide sequence will have at least about 80%, more preferably at least about 90%, and most preferably at least about 95% polynucleotide sequence identity to the polynucleotide sequence encoding HCID. A particular aspect of the invention encompasses a variant of SEQ ID NO:2 which has about 80%, more preferably at least about 90%, and most preferably at least about 95% polynucleotide sequence identity to SEQ ID NO:2.

It will be appreciated by those skilled in the art that as a result of the degeneracy of the genetic code, a multitude of nucleotide sequences encoding HCID, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring HCID, and all such variations are to be considered as being specifically disclosed.

Although nucleotide sequences which encode HCID and its variants are preferably capable of hybridizing to the nucleotide sequence of the naturally occurring HCID under appropriately selected conditions of stringency, it may be advantageous to produce nucleotide sequences encoding HCID or its derivatives possessing a substantially different codon usage. Codons may be selected to increase the rate at which expression of the peptide occurs in a particular prokaryotic or eukaryotic host in accordance with the frequency with which particular codons are utilized by the host.

Other reasons for substantially altering the nucleotide sequence encoding HCID and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode HCID and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding HCID or any fragment thereof.

Also encompassed by the invention are polynucleotide sequences that are capable of hybridizing to the claimed nucleotide sequences, and in particular, those shown in SEQ ID NO:2, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, SEQUENASE (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE amplification system marketed by Gibco/BRL (Gaithersburg, Md.). Preferably, the process is automated with machines such as the MICROLAB 2200 (Hamilton, Reno, Nev.), Peltier PTC 200 thermal cycler (MJ Research, Watertown, Mass.), and the ABI CATALYST and 373 and 377 DNA sequencers (Perkin Elmer).

The nucleic acid sequences encoding HCID may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 primer analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HCID may be used in recombinant DNA molecules to direct expression of HCID, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express HCID.

As will be understood by those of skill in the art, it may be advantageous to produce HCID-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter HCID encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding HCID may be ligated to a heterologous sequence to encode a fusion protein. For example, to screen peptide libraries for inhibitors of HCID activity, it may be useful to encode a chimeric HCID protein that can be recognized by a commercially available antibody. A fusion protein may also be engineered to contain a cleavage site located between the HCID encoding sequence and the heterologous protein sequence, so that HCID may be cleaved and purified away from the heterologous moiety.

In another embodiment, sequences encoding HCID may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of HCID, or a fragment thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, W H Freeman and Co., New York, N.Y.). The composition of the synthetic peptides may be confirmed by amino acid analysis or sequencing (e.g., the Edman degradation procedure; Creighton, supra). Additionally, the amino acid sequence of HCID, or any part thereof, may be altered during direct synthesis and/or combined using chemical methods with sequences from other proteins, or any part thereof, to produce a variant polypeptide.

In order to express a biologically active HCID, the nucleotide sequences encoding HCID or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding HCID and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding HCID. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HCID, vectors based on SV40 or EBV may be used with an appropriate selectable marker.

In bacterial systems, a number of expression vectors may be selected depending upon the use intended for HCID. For example, when large quantities of HCID are needed for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding HCID may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomvces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding HCID may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express HCID. For example, in one such system, *Autographa californica* nuclear polyhedrosis virus (AcNPV) is used as a vector to express foreign genes in *Spodoptera frugiperda* cells or in Trichoplusia larvae. The sequences encoding HCID may be cloned into a non-essential region of the virus, such as the polyhedrin gene, and placed under control of the polyhedrin promoter. Successful insertion of HCID will render the polyhedrin gene inactive and produce recombinant virus lacking coat protein. The recombinant viruses may then be used to infect, for example, *S. frugiperda* cells or Trichoplusia larvae in which HCID may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding HCID may be ligated into an adenovirus transcription/translation complex consisting of the late promoter and tripartite leader sequence. Insertion in a non-essential E1 or E3 region of the viral genome may be used to obtain a viable virus which is capable of expressing HCID in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding HCID. Such signals include the ATG initiation codon and adjacent sequences. In cases where sequences encoding HCID, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express HCID may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in $tk^-$ or $aprt^-$ cells, respectively. Also, antimetabolite, antibiotic or herbicide resistance can be used as the basis for selection; for example, dhfr, which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding HCID is inserted within a marker gene sequence, transformed cells containing sequences encoding HCID can be identified by the absence of marker gene function. Alternatively, a marker gene can be placed in tandem with a sequence encoding HCID under the control of a single promoter. Expression of the marker gene in response to induction or selection usually indicates expression of the tandem gene as well.

Alternatively, host cells which contain the nucleic acid sequence encoding HCID and express HCID may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding HCID can be detected by DNA-DNA or DNA-RNA hybridization or amplification using probes or fragments or fragments of polynucleotides encoding HCID. Nucleic acid amplification based assays involve the use of oligonucleotides or oligomers based on the sequences encoding HCID to detect transformants containing DNA or RNA encoding HCID.

A variety of protocols for detecting and measuring the expression of HCID, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on HCID is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HCID include oligolabeling, nick translation, end-labeling or PCR amplification using a labeled nucleotide. Alternatively, the sequences encoding HCID, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn (Kalamazoo, Mich.); Promega (Madison, Wis.); and U.S. Biochemical Corp. (Cleveland, Ohio)). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding HCID may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode HCID may be designed to contain signal sequences which direct secretion of HCID through a prokaryotic or eukaryotic cell membrane. Other constructions may be used to join sequences encoding HCID to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and HCID may be used to facilitate purification. One such expression vector provides for expression of a fusion protein containing HCID and a nucleic acid encoding 6 histidine residues preceding a thioredoxin or an enterokinase cleavage site. The histidine residues facilitate purification on IMIAC (immobilized metal ion affinity chromatography), as described in Porath, J. et al. (1992, Prot. Exp. Purif. 3: 263–281), while the enterokinase cleavage site provides a means for purifying HCID from the fusion protein. A discussion of vectors which contain fusion proteins is provided in Kroll, D. J. et al. (1993; DNA Cell Biol. 12:441–453).

In addition to recombinant production, fragments of HCID may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using the Applied Biosystems 431A peptide synthesizer (Perkin Elmer). Various fragments of HCID may be chemically synthesized separately and combined using chemical methods to produce the full length molecule.

Therapeutics

Chemical and structural homology exists among HCID, mPICD (GI 872121), and mICD (GI 706839)]. HCID is expressed in cancer and in reproductive tissues. In addition, HCID generates NADP which is essential for numerous cellular functions, including biosynthetic pathways of peroxisomes. Therefore, HCID appears to play a role in cancer, reproductive disorders, and disorders of peroxisome metabolism.

In one embodiment, an antagonist of HCID may be administered to a subject to prevent or treat a cancer. Such cancers may include, but are not limited to adenocarcinoma, leukemia, lymphoma, melanoma, myeloma, sarcoma, and teratocarcinoma, and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds HCID may be used directly as an antagonist or indirectly as a targeting or delivery mechanism for bringing a pharmaceutical agent to cells or tissue which express HCID.

In an additional embodiment, a vector expressing the complement of the polynucleotide encoding HCID may be administered to a subject to treat or prevent a cancer including, but not limited to, those described above.

In another embodiment, an antagonist of HCID may be administered to a subject to prevent or treat a reproductive disorder. Such disorders may include, but are not limited to, disorders of prolactin production; infertility, including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, autoimmune disorders, ectopic pregnancy, and teratogenesis; cancer of the breast, fibrocystic breast disease, and galactorrhea; disruptions of spermatogenesis, abnormal sperm physiology, cancer of the testis, cancer of the prostate, benign prostatic hyperplasia, and prostatitis, carcinoma of the male breast and gynecomastia. In one aspect, an antibody which specifically binds HCID may be used directly as an antagonist or indirectly as a targeting or delivery mechanism for bringing a pharmaceutical agent to cells or tissue which express HCID.

In an additional embodiment, a vector expressing the complement of the polynucleotide encoding HCID may be administered to a subject to treat or prevent a reproductive disorder including, but not limited to, those described above.

In another embodiment, HCID or a fragment or derivative thereof may be administered to a subject to treat or prevent a disorder of peroxisome metabolism. Such disorders include, but are not limited to, infantile Refsum disease, neonatal adrenoleukodystrophy, rhizomelic chondrodysplasia punctata X-linked adrenoleukodystrophy, and Zellweger syndrome.

In another embodiment, a vector capable of expressing HCID or a fragment or derivative thereof may be administered to a subject to treat or prevent a disorder of peroxisome metabolism including, but not limited to, those described above.

In a further embodiment, a pharmaceutical composition comprising a substantially purified HCID in conjunction with a suitable pharmaceutical carrier may be administered to a subject to treat or prevent a disorder of peroxisome metabolism including, but not limited to, those provided above.

In still another embodiment, an agonist which modulates the activity of HCID may be administered to a subject to treat or prevent a disorder of peroxisome metabolism including, but not limited to, those listed above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HCID may be produced using methods which are generally known in the art. In particular, purified HCID may be used to produce antibodies or to screen libraries of pharmaceutical agents to identify those which specifically bind HCID.

Antibodies to HCID may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with HCID or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HCID have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of HCID amino acids may be fused with those of another protein such as keyhole limpet hemocyanin and antibody produced against the chimeric molecule.

Monoclonal antibodies to HCID may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce HCID-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for HCID may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HCID and its specific antibody. A two-site, monoclonal-based immunoassay utilizing monoclonal antibodies reactive to two non-interfering HCID epitopes is preferred, but a competitive binding assay may also be employed (Maddox, supra).

In another embodiment of the invention, the polynucleotides encoding HCID, or any fragment or complement thereof, may be used for therapeutic purposes. In one aspect, the complement of the polynucleotide encoding HCID may be used in situations in which it would be desirable to block the transcription of the mRNA. In particular, cells may be transformed with sequences complementary to polynucleotides encoding HCID. Thus, complementary molecules or fragments may be used to modulate HCID activity, or to achieve regulation of gene function. Such technology is now well known in the art, and sense or antisense oligonucleotides or larger fragments, can be designed from various locations along the coding or control regions of sequences encoding HCID.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding HCID. These techniques are described both in Sambrook et al. (supra) and in Ausubel et al. (supra).

Genes encoding HCID can be turned off by transforming a cell or tissue with expression vectors which express high levels of a polynucleotide or fragment thereof which encodes HCID. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding HCID (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding HCID.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HCID. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or by polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of HCID, antibodies to HCID, mimetics, agonists, antagonists, or inhibitors of HCID. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of HCID, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example HCID or fragments thereof, antibodies of HCID, agonists, antagonists or inhibitors of HCID, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of therapeutic and toxic effects is the therapeutic index, which can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HCID may be used for the diagnosis of conditions or diseases characterized by expression of HCID, or in assays to monitor patients being treated with HCID, agonists, antagonists or inhibitors. The antibodies useful for diagnostic purposes may be prepared in the same manner as those described above for therapeutics. Diagnostic assays for HCID include methods which utilize the antibody and a label to detect HCID in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring HCID are known in the art and provide a basis for diagnosing altered or abnormal levels of HCID expression. Normal or standard values for HCID expression are established by combining body fluids or cell extracts taken from normal mammalian subjects, preferably human, with antibody to HCID under conditions suitable for complex formation. The amount of standard complex formation may be quantified by various methods, preferably by photometric means. Quantities of HCID expressed in subject samples from biopsied tissues are compared with the standard values. Deviation between standard and subject values establishes the parameters for diagnosing disease.

In another embodiment of the invention, the polynucleotides encoding HCID may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HCID may be correlated with disease. The diagnostic assay may be used to distinguish between absence, presence, and excess expression of HCID, and to monitor regulation of HCID levels during therapeutic intervention.

In one aspect, hybridization with PCR probes which are capable of detecting polynucleotide sequences, including genomic sequences, encoding HCID or closely related molecules, may be used to identify nucleic acid sequences which encode HCID. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding HCID, alleles, or related sequences.

Probes may also be used for the detection of related sequences, and should preferably contain at least 50% of the nucleotides from any of the HCID encoding sequences. The hybridization probes of the subject invention may be DNA or RNA and derived from the nucleotide sequence of SEQ ID NO:2 or from genomic sequence including promoter, enhancer elements, and introns of the naturally occurring HCID.

Means for producing specific hybridization probes for DNAs encoding HCID include the cloning of nucleic acid sequences encoding HCID or HCID derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding HCID may be used for the diagnosis of conditions or disorders which are associated with expression of HCID. Examples of such conditions or disorders include cancers, such as adenocarcinoma, leukemia, lymphoma, melanoma, mycloma, sarcoma, and teratocarcinoma, and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; reproductive disorders, such as disorders of prolactin production; infertility, including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, autoimmune disorders, ectopic pregnancy, and teratogenesis; cancer of the breast, fibrocystic breast disease, and galactorrhea; disruptions of spermatogenesis, abnormal sperm physiology, cancer of the testis, cancer of the prostate, benign prostatic hyperplasia, and prostatitis, carcinoma of the male breast and gynecomastia; and disorders of peroxisome metabolism, such as infantile Refsum disease, neonatal adrenoleukodystrophy, rhizomelic chondrodysplasia punctata X-linked adrenoleukodystrophy, and Zellweger syndrome. The polynucleotide sequences encoding HCID may be used in Southern or northern analysis, dot blot, or other membrane-based technologies; in PCR technologies; or in dipstick, pin, ELISA assays or microarrays utilizing fluids or tissues from patient biopsies to detect altered HCID expression. Such qualitative or quantitative methods are well known in the art.

In a particular aspect, the nucleotide sequences encoding HCID may be useful in assays that detect activation or induction of various cancers, particularly those mentioned above. The nucleotide sequences encoding HCID may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding HCID in the sample indicates the presence of the associated disease. Such assaparticular therapeutic treluate the efficacy of a particular therapeutic treatment regimen in animal studies, in clinical trials, or in monitoring the treatment of an individual patient.

In order to provide a basis for the diagnosis of disease associated with expression of HCID, a normal or standard profile for expression is established. This may be accomplished by combining body fluids or cell extracts taken from normal subjects, either animal or human, with a sequence, or a fragment thereof, which encodes HCID, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HCID may involve the use of PCR. Such oligomers may be chemically synthesized, generated enzymatically, or produced in vitro. Oligomers will preferably consist of two nucleotide sequences, one with sense orientation (5'->3') and another with antisense (3'<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of HCID include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 212: 229–236). The speed of quantitation of multiple samples may be accelerated by running the assay in an ELISA format where the oligomer of interest is presented in various dilutions and a spectrophotometric or colorimetric response gives rapid quantitation.

In further embodiments, an oligonucleotide derived from any of the polynucleotide sequences described herein may be used as a target in a microarray. The microarray can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents (Heller, R. et al. (1997) Proc. Natl. Acad. Sci. 94:2150–55).

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides which are only 7–10 nucleotides in length. The microarray may contain oligonucleotides which cover the known 5', or 3', sequence, sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode HCID may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding HCID on a physical chromosomal map and a specific disease , or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, HCID, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between HCID and the agent being tested, may be measured.

Another technique for drug screening which may be used provides for high throughput screening of compounds having suitable binding affinity to the protein of interest as described in published PCT application WO84/03564. In this method, as applied to HCID large numbers of different small test compounds are synthesized on a solid substrate, such as plastic pins or some other surface. The test compounds are reacted with HCID, or fragments thereof, and washed. Bound HCID is then detected by methods well known in the art. Purified HCID can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HCID specifically compete with a test compound for binding HCID. In this manner, the antibodies can be used to detect the presence of any peptide which shares one or more antigenic determinants with HCID.

In additional embodiments, the nucleotide sequences which encode HCID may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I BRSTTUT03 cDNA Library Construction

The BRSTTUT03 cDNA library was constructed from cancerous breast tissue removed from a 58-year-old Caucasian female who had undergone unilateral extended simple mastectomy following diagnosis of multicentric invasive grade 4 mammary lobular carcinoma. The pathology report indicated that tumor cells were identified in the upper outer quadrant of the left breast, forming a single predominant mass. Tumor cells were also identified in the lower outer quadrant of the left breast, forming three separate nodules. The surgical margins were found negative for tumor. The skin, nipple, and fascia were uninvolved. No evidence of vascular invasion was found. Eight mid low and two high left axillary lymph nodes were found negative for tumor. Prior to surgery, the patient was diagnosed with skin cancer, cerebrovascular disease, atherosclerosis, rheumatic heart disease, and osteoarthritis. The patient family history included breast cancer in patient's mother and prostate cancer in patient's brother.

The frozen tissue was homogenized and lysed using a POLYTRON PT-3000 homogenizer (Brinkmann Instruments, Westbury, N.J.) in guanidinium isothiocyanate solution. The lysate was centrifuged over a 5.7M CsCl cushion using an SW28 rotor in an L8-70M ultracentrifuge (Beckman Instruments) for 18 hours at 25,000 rpm at ambient temperature. The RNA was extracted with acid phenol pH 4.7, precipitated using 0.3M sodium acetate and 2.5 volumes of ethanol, resuspended in RNAse-free water, and DNase treated at 37° C. The RNA extraction was repeated with acid phenol pH 4.7 and precipitated with sodium acetate and ethanol as before. The mRNA was then isolated using the OLIGOTEX kit (QIAGEN, Inc., Chatsworth, Calif.) and used to construct the cDNA library.

The mRNA was handled according to the recommended protocols in the SUPERSCRIPT plasmid system for cDNA synthesis and plasmid cloning (Cat. #18248-013; Gibco/BRL). cDNAs were fractionated on a SEPHAROSE CL4B column (Cat. #275105-01; Pharmacia), and those cDNAs exceeding 400 bp were ligated into PSPORT1. The plasmid PSPORT1 was subsequently transformed into DH12S competent cells (Cat. #18312-017; Gibco/BRL).

II Isolation and Sequencing of cDNA Clones

Plasmid DNA was released from the cells and purified using the R.E.A.L. PREP 96 plasmid kit (Catalog #26173; QIAGEN, Inc.). The recommended protocol was employed except for the following changes: 1) the bacteria were cultured in 1 ml of sterile Terrific Broth (Catalog #22711, Gibco/BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

Alternative methods of purifying plasmid DNA include the use of the MAGIC MINIPREPS DNA purification system (Cat. No. A7100, Promega) or QIAWELL-8 plasmid QIAWELL PLUS DNA, and QIAWELL ULTRA DNA purification systems (Qiagen, Inc.).

The cDNAs were sequenced by the method of Sanger F. and A. R. Coulson (1975; J. Mol. Biol. 94: 441f), using a MICROLAB 2200 (Hamilton, Reno Nev.) in combination with four Peltier PTC200 thermal cyclers (MJ Research, Watertown Mass.) and Applied Biosystems 377 or 373 DNA sequencing systems (Perkin Elmer) and reading frame was determined.

III Homology Searching of cDNA Clones and Their Deduced Proteins

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul SF (1993) J Mol Evol 36:290–300; Altschul, SF et al (1990) J Mol Biol 215:403–10).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith, R. F. and T. F. Smith (1992; Protein Engineering 5:35–51), incorporated herein by reference, can be used when dealing with primary sequence patterns and secondary structure gap penalties. As disclosed in this application, sequences have lengths of at least 49 nucleotides and no more than 12% uncalled bases (where N is recorded rather than A, C, G, or T).

The BLAST approach, as detailed in Karlin and Altschul (1993; Proc Nat Acad Sci 90:5873–7) and incorporated herein by reference, searches matches between a query sequence and a database sequence, to evaluate the statistical significance of any matches found, and to report only those matches which satisfy the user-selected threshold of significance. In this application, threshold is set at 10–25 for nucleotides and 10–14 for peptides.

Incyte nucleotide sequences were searched against the GenBank databases for primate (pri), rodent (rod), and other mammalian sequences (mam); and deduced amino acid sequences from the same clones were then searched against GenBank functional protein databases, mammalian (mamp), vertebrate (vrtp), and eukaryote (eukp) for homology.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. (1993) *J. Mol. Evol.* 36:290–300; Altschul, S. F. et al. (1990) *J. MOL. EVOL.* 215:403–410) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\%\text{ sequence identity} \times \%\text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding HCID occurs. Abundance and percent abundance are also reported. Abundance directly reflects the number of times a particular transcript is represented in a cDNA library, and percent abundance is abundance divided by the total number of sequences examined in the cDNA library.

V Extension of HCID Encoding Polynucleotides

The nucleic acid sequence of the Incyte Clone 1996789 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence “outward” generating amplicons containing new, unknown nucleotide sequence for the region of interest. The initial primers were designed from the cDNA using OLIGO 4.06 software (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Gibco/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier PTC200 thermal cycler (M.J. Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQUICK (QIAGEN Inc., Chatsworth, Calif.), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2–3 hours or overnight at 16° C. Competent *E. coli* cells (in 40 μl of appropriate media) were transformed with 3 μl of ligation mixture and cultured in 80 μl of SOC medium (Sambrook et al., supra). After incubation for one hour at 37° C., the *E. coli* mixture was plated on Luria Bertani (LB)-agar (Sambrook et al., supra) containing 2× Carb. The following day, several colonies were randomly picked from each plate and cultured in 150 μl of liquid LB/2× Carb medium placed in an individual well of an appropriate, commercially-available, sterile 96-well microtiter plate. The following day, 5 μl of each overnight culture was transferred into a non-sterile 96-well plate and after dilution 1:10 with water, 5 μl of each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 software (National Biosciences), labeled by combining 50 pmol of each oligomer and 250 $\mu$Ci of [$\gamma$-$^{32}$P] adenosine triphosphate (Amersham) and T4 polynucleotide kinase (DuPont NEN®, Boston, Mass.). The labeled oligonucleotides are substantially purified with SEPHADEX G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN).

The DNA from each digest is fractionated on a 0.7 percent agarose gel and transferred to nylon membranes (NYTRAN Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR film (Kodak, Rochester, N.Y.) is exposed to the blots or the blots are exposed to a Phosphoimager cassette (Molecular Dynamics, Sunnyvale, Calif.), hybridization patterns are compared visually.

VII Microarrays

To produce oligonucleotides for a microarray, the nucleotide sequence described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the micro-array.

VIII Complementary Polynucleotides

Sequence complementary to the HCID-encoding sequence, or any part thereof, is used to decrease or inhibit expression of naturally occurring HCID. Although use of oligonucleotides comprising from about 15 to about 30 base-pairs is described, essentially the same procedure is used with smaller or larger sequence fragments. Appropriate oligonucleotides are designed using OLIGO 4.06 software and the coding sequence of HCID, SEQ ID NO:1. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HCID-encoding transcript.

IX Expression of HCID

Expression of HCID is accomplished by subcloning the cDNAs into appropriate vectors and transforming the vectors into host cells. In this case, the cloning vector is also used to express HCID in *E. coli.* Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of HCID into the bacterial growth media which can be used directly in the following assay for activity.

X Demonstration of HCID Activity

The activity of HCID in a sample is determined by measuring the change in absorbance at 340 nm following HCID-catalyzed reduction of NADP to NADPH. An enzyme sample is incubated with NADP (the oxidized form), in 0.1M Tris/HCl, pH 8, 3 mM $MgCl_2$. Addition of isocitrate starts the reaction, which generates NADPH (th reduced form) which no longer absorbs at 340 nm. This change in absorbance following the addition of isocitrate is proportional to the activity of HCID in the sample (Jennings G. T. and Stevenson P. M. (1991) supra).

XI Production of HICID Specific Antibodies

HCID that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems 431A peptide synthesizer using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring HCID Using Specific Antibodies

Naturally occurring or recombinant HCID is substantially purified by immunoaffinity chromatography using antibodies specific for HCID. An immunoaffinity column is constructed by covalently coupling HCID antibody to an activated chromatographic resin, such as CNBr-activated SEPHAROSE (Pharmacia & Upjohn). After the coupling, the resin is blocked and washed according to the manufacturer's instructions.

Media containing HCID is passed over the immunoaffinity column, and the column is washed under conditions that allow the preferential absorbance of HCID (e.g., high ionic strength buffers in the presence of detergent). The column is eluted under conditions that disrupt antibody/HCID binding (e.g., a buffer of pH 2–3 or a high concentration of a chaotrope, such as urea or thiocyanate ion), and HCID is collected.

XIII Identification of Molecules Which Interact with HCID

HCID or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled HCID, washed and any wells with labeled HCID complex are assayed. Data obtained using different concentrations of HCID are used to calculate values for the number, affinity, and association of HCID with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide sequence encoding a polypeptide comprising the amino acid sequence of SEQ ID:1.

2. A composition comprising the polynucleotide sequence of claim 1.

3. An isolated and purified polynucleotide sequence which is fully complementary to the polynucleotide sequence of claim 1.

4. An isolated and purified polynucleotide sequence consisting of SEQ ID NO:2.

5. An isolated and purified polynucleotide sequence which is fully complementary to the polynucleotide sequence of claim 4.

6. An expression vector containing the polynucleotide sequence of claim 1.

7. A host cell containing the expression vector of claim 6.

8. A method for detecting a polynucleotide encoding a polypeptide comprising the amino acid sequence of SEQ ID NO:1 in a biological sample containing nucleic acid material, the method comprising the steps of:

(a) hybridizing the polynucleotide of claim 3 to the nucleic acid material of the biological sample, thereby forming a hybridization complex; and (b) detecting the hybridization complex, wherein the presence of the hybridization complex correlates with the presence of the polynucleotide encoding the polypeptide in the biological sample.

9. The method of claim 8 wherein the nucleic acid material is amplified by the polymerase chain reaction prior to the hybridizing step.

* * * * *